(12) United States Patent
Kraus (10) Patent No.: US 7,235,060 B2
(45) Date of Patent: Jun. 26, 2007

(54) HYDROCEPHALUS SHUNT SYSTEM WITH ENDOSCOPIC PLACEMENT FEATURES

(75) Inventor: Robert G. Kraus, Attleboro, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 340 days.

(21) Appl. No.: 10/400,730

(22) Filed: Mar. 27, 2003

(65) Prior Publication Data
US 2004/0193094 A1   Sep. 30, 2004

(51) Int. Cl.
*A61M 5/00* (2006.01)
*A61M 25/00* (2006.01)

(52) U.S. Cl. .............................. 604/9; 604/8; 604/264; 604/175; 606/108

(58) Field of Classification Search .............. 604/7–10, 604/65–67, 131, 151, 264, 533, 247, 175; 606/108
See application file for complete search history.

(56) References Cited

U.S. PATENT DOCUMENTS

| | | | |
|---|---|---|---|
| 3,886,948 A | 6/1975 | Hakim | |
| 4,332,255 A | 6/1982 | Hakim et al. | |
| 4,387,715 A | 6/1983 | Hakim et al. | |
| 4,551,128 A | 11/1985 | Hakim et al. | |
| 4,578,057 A | 3/1986 | Sussman | |
| 4,595,390 A | 6/1986 | Hakim et al. | |
| 4,615,691 A | 10/1986 | Hakim et al. | |
| 4,772,257 A | 9/1988 | Hakim et al. | |
| 4,963,133 A * | 10/1990 | Whipple | 604/533 |
| 5,167,615 A * | 12/1992 | East et al. | 604/9 |
| 5,176,627 A | 1/1993 | Watson | |
| 5,304,114 A | 4/1994 | Cosman | |
| 5,385,541 A | 1/1995 | Kirsch et al. | |
| 5,387,188 A | 2/1995 | Watson | |
| 5,437,626 A | 8/1995 | Cohen et al. | |
| 5,458,606 A | 10/1995 | Cohen et al. | |
| 5,637,083 A * | 6/1997 | Bertrand et al. | 604/9 |
| 5,713,858 A | 2/1998 | Heruth et al. | |
| 5,800,376 A * | 9/1998 | Watson et al. | 604/9 |
| 5,928,182 A | 7/1999 | Kraus et al. | |
| 6,203,513 B1 * | 3/2001 | Yaron et al. | 604/9 |
| 6,666,208 B1 * | 12/2003 | Schumacher et al. | 128/200.24 |

FOREIGN PATENT DOCUMENTS

| | | |
|---|---|---|
| DE | 3603463 | 8/1987 |
| EP | 0270205 | 6/1988 |
| EP | 0366389 | 5/1990 |
| JP | 07308285 | 11/1995 |
| JP | 09225039 | 9/1997 |

\* cited by examiner

*Primary Examiner*—Tatyana Zalukaeva
*Assistant Examiner*—Leslie R. Deak
(74) *Attorney, Agent, or Firm*—Nutter, McClennen & Fish LLP (57) ABSTRACT

A shunt system for controlling the flow of fluid from one region of a patient to a different region of the patient's body. The shunt system includes endoscopic placement features so that the system can be placed endoscopically in a minimally invasive surgery. Also provided is a single fluid flow control device having flow control characteristics previously obtainable only by connecting in series two or more shunt system components. In addition, the shunt system includes a selectively engageable locking mechanism that allows the system to be assembled quickly and easily, without the need for sutures or adhesives. The present assembly process minimizes the possibility of any unintended fluid leakage from the device.

26 Claims, 7 Drawing Sheets

DISTAL PUMPING OR ANTI-REFLUX

FIG. 4

NORMAL ERECT FLOW

FIG. 5A

ENDOSCOPIC PLACEMENT OR VENTRICULAR INJECTION

FIG. 5B

DISTAL PUMPING OR ANTI-REFLUX

FIG. 6A

NORMAL ERECT FLOW

FIG. 6B

ANTI-SIPHON FLOW

FIG. 6C

PRONE FLOW

FIG. 6D

ENDOSCOPIC PLACEMENT OR VENTRICULAR INJECTION

HYDROCEPHALUS SHUNT SYSTEM WITH ENDOSCOPIC PLACEMENT FEATURES

CROSS-REFERENCE TO RELATED APPLICATIONS

Not applicable.

STATEMENT REGARDING FEDERALLY SPONSORED RESEARCH

Not Applicable.

FIELD OF THE INVENTION

The present invention relates to medical devices for directing bodily fluids from one region of a patient to another region. More specifically, this invention relates to a shunt system having endoscopic placement features that allow its minimally invasive placement within a patient, and apparatus to facilitate such endoscopic placement.

BACKGROUND OF THE INVENTION

Hydrocephalus is a condition afflicting patients who are unable to regulate cerebrospinal fluid flow through their body's own natural pathways. Produced by the ventricular system, cerebrospinal fluid is normally absorbed by the body's venous system. In a patient suffering from hydrocephalus, the cerebrospinal fluid is not absorbed in this manner, but instead accumulates in the ventricles of the patient's brain. If left untreated, the increasing volume of fluid elevates the patient's intracranial pressure and can lead to serious medical conditions such as subdural hematoma, compression of the brain tissue, and impaired blood flow.

The treatment of hydrocephalus has conventionally involved draining the excess fluid away from the ventricles and rerouting the cerebrospinal fluid to another area of the patient's body, such as the abdomen or vascular system. A drainage system, commonly referred to as a shunt, is often used to carry out the transfer of fluid. In order to install the shunt, typically a scalp incision is made and a small hole is drilled in the skull. The proximal end of the shunt, which usually includes a proximal, or ventricular, catheter, is installed in the ventricular cavity of the patient's brain. The distal end of the shunt, which includes a distal, or drainage, catheter, is installed in that portion of the patient's body where the excess fluid is to be reintroduced. To regulate the flow of cerebrospinal fluid and maintain the proper pressure in the ventricles, a pump or valve can be placed between the proximal and distal catheters. If the pump or valve is not equipped with anti-siphon features and such features are desirable, a siphon control device can be separately included. The siphon control device can be positioned within the fluidic pathway, usually between the shunt valve and the drainage catheter. The siphon control device avoids overdrainage caused by the siphoning effect of hydrostatic pressure in the distal shunt catheter, which can be created by the elevation of the proximal catheter inlet with respect to the distal catheter outlet, i.e., when the patient sits or stands.

In most conventional shunt systems, the various components that form the shunt system, i.e., proximal and distal catheters, shunt valve, anti-siphon device, tubing, etc., are manufactured separately and then connected together during implantation to form the complete drainage pathway. During a typical surgical procedure, the proximal catheter is inserted directly into the ventricle cavity, after which the shunt valve and a pre-attached distal catheter are then implanted near the surface of the skull at an approximately 90° angle with respect to the proximal catheter. The proximal catheter is then attached by means of suturing surgical tubing to an inlet port on the shunt valve, thereby forming a right angle with respect to the shunt valve. With the current increase in popularity of endoscopic surgeries, some neurosurgeons have now attempted rigid endoscopic placement of ventricular catheters into the ventricles of the brain. In some cases endoscopic placement of shunt valves having domed silicone reservoirs with attached pre-cut catheters has even been attempted.

Because of the limited space available for the surgeon to perform the suturing after the proximal catheter is advanced into the ventricles, the assembly procedure after endoscopic implantation of the shunt system components can be extremely difficult. Also, shunts having domed reservoirs are not easily occluded for flushing distally. Given the amount of time necessary to suture the surgical tubing that connects the ventricular catheter to the shunt valve, the length of the surgical procedure can prove to be less than desirable. An added setback to using these conventional shunt systems is the compatibility problems that arise when the various components are produced by different manufacturers. Furthermore, currently available shunt systems can be prone to shunt separation and/or leakage at the sites where the separate components are connected to one another via the surgical tubing.

SUMMARY OF THE INVENTION

The present invention provides a shunt system for controlling the flow of fluid from one region of a patient to a different region of the patient's body. The shunt system includes endoscopic placement features so that the system can be placed endoscopically for implantation in a minimally invasive surgery. Also provided is a single, fluid flow control device having flow control characteristics previously obtainable only by connecting in series two or more shunt system components. In addition, the shunt system can be assembled quickly and easily, without the need for suturing. The present assembly process minimizes the possibility of any unintended fluid leakage from the device, and preferably requires no adhesive to secure any of the components forming the shunt system to one another.

In an exemplary embodiment of the present invention, the shunt system comprises a shunt device contained within a housing. The shunt device is comprised of a valve mechanism for regulating fluid flow into and out of the shunt system, a pump chamber in fluid communication with the valve mechanism, and a reservoir which is also connected to and in fluid communication with the pump chamber. The reservoir includes a top section and a base section that terminates in a catheter connector. At least a portion of the connector extends out of the housing, and in one exemplary embodiment both the base section including the connector extends out of the housing. The shunt system also includes an inflow catheter and an outflow catheter, each catheter having first and second ends, and a channel extending between the first and second ends for carrying fluid within the catheter. The first end of each catheter is configured as an attachment end for connection to the shunt device to thereby form a fluidic pathway for transferring fluid from one region of the patient to another region. The second end of the inflow catheter serves as the fluid uptake end of the shunt system (i.e., where fluid enters the system), while the second end of the outflow catheter serves as the fluid release end of the shunt system (i.e., where fluid exits the system.) In addition, the first end of the inflow catheter is configured to be secured to the connector of the reservoir, and can include a locking mechanism for maintaining the attachment end around the connector.

In one aspect of the present invention, the connector includes a flange while the inflow catheter includes an attachment end that fits over the flange. The inner diameter of the attachment end is configured to be slightly smaller than the largest outer diameter of the flange, thereby enabling an interference fit to be formed when the attachment end is urged over the connector and flange. Included with the inflow catheter is a selectively engageable locking mechanism that is adapted to secure the attachment end of the inflow catheter to the connector. The locking mechanism comprises a retaining ring for maintaining the attachment end of the inflow catheter onto the connector. Once fully assembled, the inflow catheter extends at approximately 90° with respect to the outflow catheter. The ventricular catheter can have either an open or a closed second end configured for fluid uptake. If the fluid uptake end is closed, a pre-slit can be provided so as to allow an endoscope to pass through the second end. A series of apertures can be provided near the second end to facilitate the entry of fluid into the catheter.

In one exemplary embodiment, the retaining ring can be provided on the inflow catheter, and can be configured to slide along the inflow catheter and towards the attachment end of the inflow catheter when the attachment end is fitted onto the connector. When advanced over the flange, the retaining ring compresses the attachment end around the flange and thereby secures the inflow catheter onto the connector. The inflow catheter can also include indicia on the outer surface of the catheter to designate corresponding lengths. The marks can aid the surgeon in pre-sizing the ventricular catheter to individual patients once the specific catheter size desired has been determined by either CT scan or other known imaging techniques. This way, the surgeon can adjust the length, i.e., by cutting the catheter to the required size, intraoperatively. After the inflow catheter has been cut to the desired size, the retaining ring can be advanced near the attachment end prior to assembly.

In another exemplary embodiment of the present invention, rather than being slidable with respect to the inflow catheter, the retaining ring can be firmly secured to the inflow catheter at the attachment end. In yet another exemplary embodiment, the retaining ring can be secured to the inner diameter of the inflow catheter at the attachment end.

In other aspects of the present invention, the reservoir can be a domed reservoir while the housing can include a domed cap for accommodating the domed reservoir. Within the reservoir, a check valve mechanism is provided in the base portion to prevent occlusion of the shunt device during pumping of the valve mechanism. The check valve mechanism can comprise a free floating ball. The reservoir also includes surface features that provide the valve mechanism with anti-siphon properties. For example, the base portion can be provided with a central flow channel that connects to peripheral flow channels. Helically arranged ridges can be included within the peripheral flow channels to provide a tortuous fluid flow pathway with greater resistance to prevent siphoning. Also, the domed cap can include an endoscope port comprising a pre-formed slit that connects to the top portion of the reservoir. The endoscope port can be formed from a resealable silicone to allow an endoscope to pass through the housing and down into the reservoir base portion itself. The endoscope port can also be radiopaque to allow easy visualization and identification. The free-floating ball of the check valve mechanism can be pushed aside or manipulated aside with the endoscope.

The present invention also provides an instrument for assembling the ventricular catheter to the shunt device. The instrument has a first arm having a proximal end including a gripping section configured for holding a portion of the housing, and a distal end including a handle portion. Pivotally connected to the first arm is a second arm which has a proximal end including a platform section configured to sit around the inflow catheter and adjacent to the retaining ring. Upon the application of force to move the handle portions towards each other, the gripping section and the platform section of the arms push against the housing and the retaining ring, sliding the retaining ring over the attachment end of the ventricular catheter and over the flange of the connector.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying drawings, in which.

DETAILED DESCRIPTION OF THE INVENTION

Figure 1A:
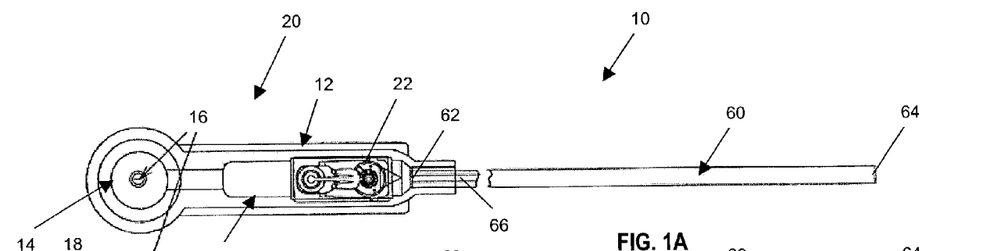
FIG. 1A is a top-down view of the shunt system of the present invention.
Figures 1B, 1C:
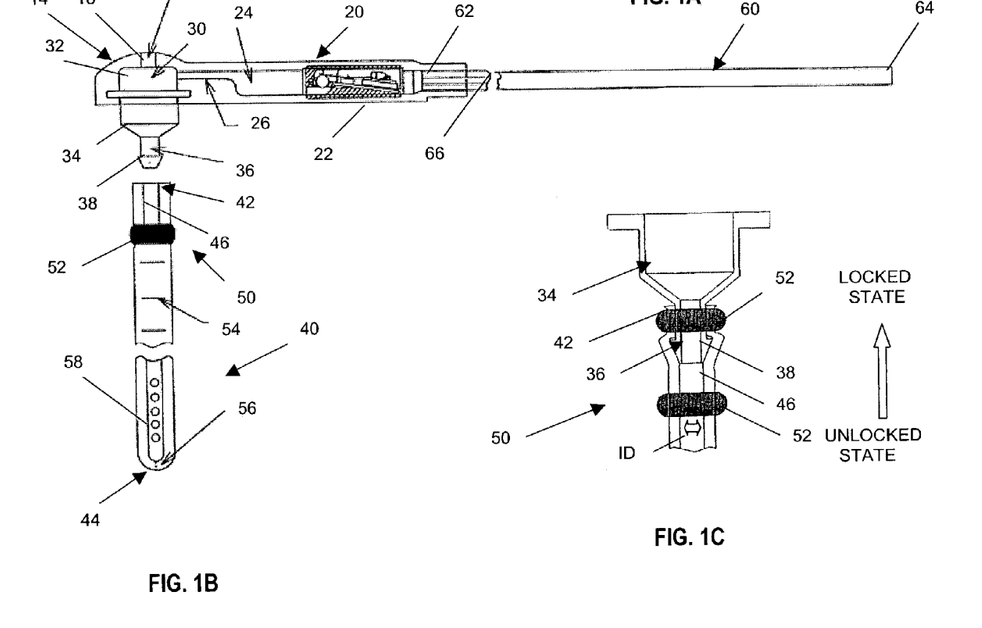
FIG. 1B is an exploded view of the shunt system of FIG. 1A.
FIG. 1C is an enlarged view of the reservoir and attached inflow catheter.

The present invention provides a shunt system having endoscopic placement features which allow the system to be surgically implanted and easily assembled using minimally invasive techniques. Turning now to the drawings and particularly to FIGS. 1A and 1B, a shunt system 10 in accordance with the present invention is shown. In an exemplary embodiment of the present invention, the shunt system 10 comprises a shunt device 20 contained within a housing 12. The shunt device 20 includes a valve mechanism 22 for regulating fluid flow into and out of the shunt device 20. The valve mechanism 22 can comprise any typical valve mechanism, such as the ball-in-cone valve illustrated and as described in U.S. Pat. Nos. 3,886,948, 4,332,255, 4,387,715, 4,551,128, 4,595,390, 4,615,691, 4,772,257, and 5,928,182, all of which are hereby incorporated by reference. Of course, it is understood that the valve mechanism 22 can also comprise other suitable valves including programmable valves for controlling fluid flow in a shunt device as are known in the art.

Figure 3:
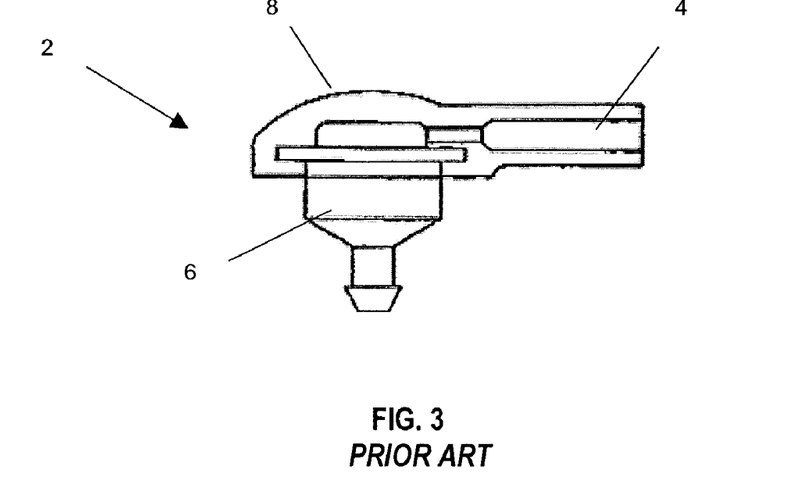
FIG. 3 is a side view of a domed reservoir of the prior art.

Also included in the shunt device 20 is a pump chamber 24 that is connected to and in fluid communication with the valve mechanism 22. The pump chamber 24 can comprise a flexible diaphragm 26 that enables selective occlusion of fluid flow into and out of the pump chamber 24, thereby allowing bidirectional pumping of fluid between the pump chamber 24 and an attached reservoir 30 that is in fluid communication with the pump chamber 24. The reservoir 30 comprises a top section 32 and a base section 34 which terminates in a catheter connector 36. A portion of the base section 34 including the connector 36 extends out of the housing 12 as shown in FIG. 1B. However, it is understood that only the connector 36 need be located outside of the housing 12 for ease of assembly, and the base section 34 itself may be wholly contained within the housing 12 if desired. The top section 32 of the reservoir 30 which connects to the pump chamber 24 serves as a second pump chamber. Preferably, the reservoir 30 can be a "domed" reservoir. That is, the top section 32 of the reservoir 30 is situated under a domed cap 14 that forms a part of the housing 12, much like in the prior art Rickham pump chamber 2 of FIG. 3 in which there is shown a pump chamber 4 attached to a reservoir 6 seated underneath a domed housing 8. In the present invention, both the top section 32 of the reservoir 30 and the pump chamber 24 are each configured to handle approximately 0.08 cc of fluid volume, thereby allowing in total about four times the fluid volume as compared to the Rickham pump chamber 2 of the prior art. However, the length of the housing 12 itself is approximately 4 cm so the overall dimensions of the shunt device 20 are still relatively small.

To form the complete fluid flow pathway, catheters 40, 60 are connected to the shunt device 20 of the present invention. Provided with the shunt system 10 is an inflow catheter 40 having a first end 42, a second end 44, and a channel 46 extending between the first end 42 and second end 44. The first end 42 of the inflow catheter 40 is configured to attach to the base section 34 of the reservoir 30 by way of the catheter connector 36, while the second end 44 serves as the fluid uptake end, thereby providing a pathway for fluid to enter the shunt system 10. In a hydrocephalus shunt system, the inflow, or ventricular, catheter 40 is placed in a ventricle of the patient so that cerebrospinal fluid can enter the shunt device 20. After the cerebrospinal fluid enters the shunt device 20, the fluid is regulated by the valve mechanism 22 and, according to the patient's physiological condition, excess cerebrospinal fluid is released from the shunt device 20 through an outflow, or drainage, catheter 60. The excess fluid is carried out through a channel 66 extending between a first end 62 of the outflow catheter 60, which first end 62 is configured to attach to the valve mechanism 22, and a second, fluid release end 64 where the fluid exits the shunt system 10.

As shown in FIG. 1B, the catheter connector 36 includes a flange 38 at its free end. The first, attachment end 42 of the inflow catheter 40 has an inner diameter ID which is slightly smaller than the largest outer diameter of the flange 38. This inner diameter ID can be the diameter of the channel 46 extending from the first, attachment end 42 to the second, fluid uptake end 44 of the inflow catheter 40 provided the channel 46 has a consistent diameter throughout the inflow catheter 40. However, it is understood that the inner diameter ID of the channel 46 need only be smaller than the largest outer diameter of the flange 38 at a section near the first, attachment end 42 of the inflow catheter 40. This smaller inner diameter ID enables the attachment end 42 to form a tight, interference fit with the connector 36 when the attachment end 42 is urged onto the connector 36 and flange 38. The inflow catheter 40 can be formed from a resilient and flexible material such as medical-grade silicone to allow the first, attachment end 42 to deform and fit over the connector 36 and flange 38 as the inflow catheter 40 is advanced towards the base section 34.

To secure the first, attachment end 42 of the inflow catheter 40 to the connector 36, a selectively engageable locking mechanism 50 is provided with the inflow catheter 40. The locking mechanism 50 can comprise a retaining ring 52 for maintaining the attachment end 42 of the inflow catheter 40 onto the connector 36. In one exemplary embodiment, the retaining ring 52 is able to move, or slide over the inflow catheter 40 and beyond the flange 38 when the inflow catheter 40 is attached to the connector 36. As illustrated in FIG. 1C, the retaining ring 52 can be situated adjacent to the attachment end 42 in an unlocked state. After the attachment end 42 is urged onto the connector 36 and flange 38, the retaining ring 52 can be moved towards the attachment end 42 such as by sliding, twisting, or other similar advancing action until the retaining ring 52 passes over the flange 38 held within the attachment end 42. In this locked state as shown, the retaining ring 52 compresses the flexible attachment end 42 over the connector 36. The retaining ring 52 is configured such that the inner diameter is smaller than the largest outer diameter of the attachment end 42 with the flange 38 therein, thereby preventing the retaining ring 52 from sliding out of its locked state back to its unlocked state.

It is contemplated that the retaining ring 52 can be formed of a suitable biocompatible material such as titanium or titanium alloy, while the connector 36 and flange 38 are formed of a semi-deformable material such as nylon to allow enough compression for the retaining ring 52 to slide over the flange 38. With this locking mechanism 50, the inflow catheter 40 is able to be assembled to the shunt device 20 quickly and easily, without the need for sutures or adhesives. The retaining ring 52 also provides a more consistent joining force than current suturing methods.

The inflow catheter 40 of the present invention also provides features that enable its customization to a particular patient. On the outer surface of the inflow catheter 40 are marks or indicia 54 which correspond to the length of the inflow catheter 40. These marks 54 can aid the surgeon in pre-sizing the inflow catheter 40 to the individual patient once the specific size of the ventricular tube needed has been determined by either CT scan or other known imaging techniques. This way, the surgeon can adjust the length, i.e., by cutting the catheter 40 to the required size, intraoperatively. If it is desirable to cut the inflow catheter 40 to size, the retaining ring 52 can be slid away from the area to be cut, near the second, fluid uptake end 44. Alternatively, the retaining ring 52 can be taken off the inflow catheter 42 entirely, and placed back on after the inflow catheter 40 has been cut to size. Once the inflow catheter 40 has been cut to the desired size, the retaining ring 52 is advanced near the first, attachment end 42 prior to assembly.

In addition, the inflow catheter 40 can have either an open or a closed second end 44 for surgeon modification to allow visualization with an endoscope. If the second end 44 is closed, a pre-formed slit 56 can be provided so as to allow the endoscope to pass through the second end 44. Since the second end 44 serves as the fluid uptake end, a series of apertures 58 can be provided near the closed second end 44 to facilitate fluid entry into the inflow catheter 40.

Figure 2A:
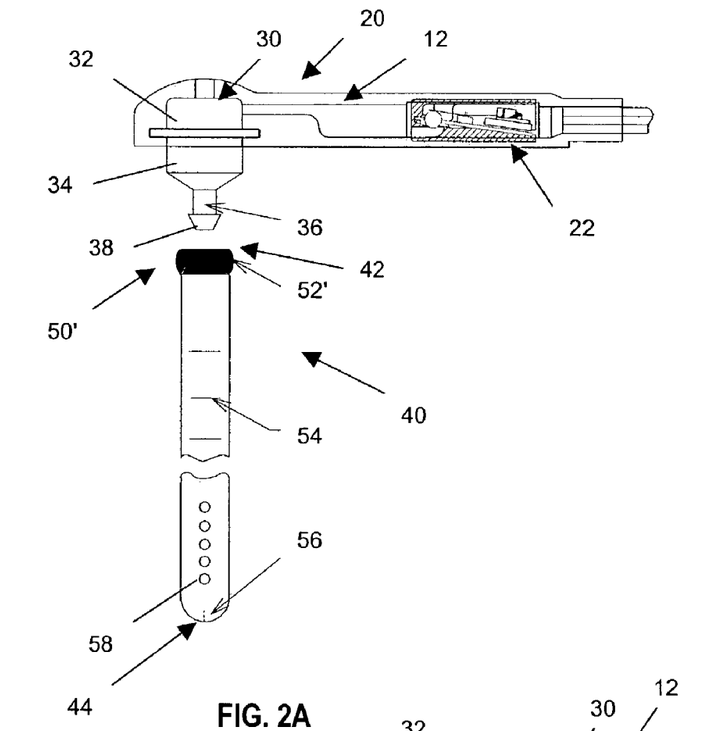
FIG. 2A is an exploded view of another embodiment of a locking mechanism and inflow catheter of the present invention.
Figure 2B:
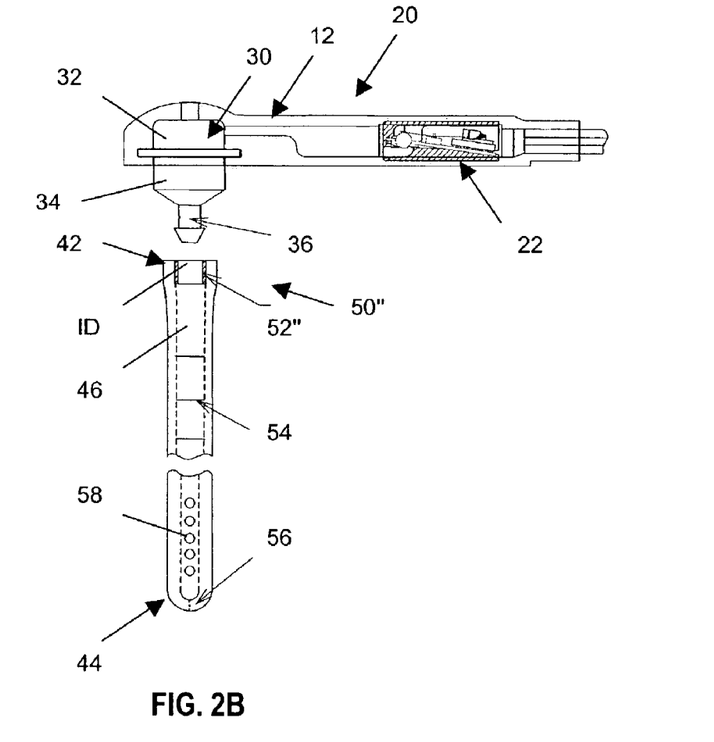
FIG. 2B is an exploded view of yet another embodiment of a locking mechanism and inflow catheter of the present invention.

Rather than having a sliding retaining ring 52 on the inflow catheter 40, FIG. 2A shows another exemplary embodiment of a locking mechanism 50' comprising a retaining ring 52' that is firmly secured to the inflow catheter 40 of the present system 10 at its attachment end 42. The retaining ring 52' can resemble the retaining ring 52 of FIGS. 1B and 1C in size, shape, and composition, except that the retaining ring 52' is bonded to the outer diameter of the inflow catheter 40. FIG. 2B shows yet another exemplary embodiment of a locking mechanism 50" for use with the inflow catheter 40 of the present system 10, in which a retaining ring 52" is firmly secured such as by bonding to the inner diameter ID of the inflow catheter 40 at its attachment end 42. The retaining ring 52" can be formed from a semi-deformable material such as nylon. The retaining rings 52', 52" of the present invention can be used with pre-cut fixed length inflow catheters 40. During assembly, the bonded retaining rings 52', 52" pop over the flange 38 of the connector 36 when the inflow catheter 40 is urged onto the connector 36, thus retaining the inflow catheter 40 and the connector 36 together without the need for sutures or adhesives.

Figure 4:
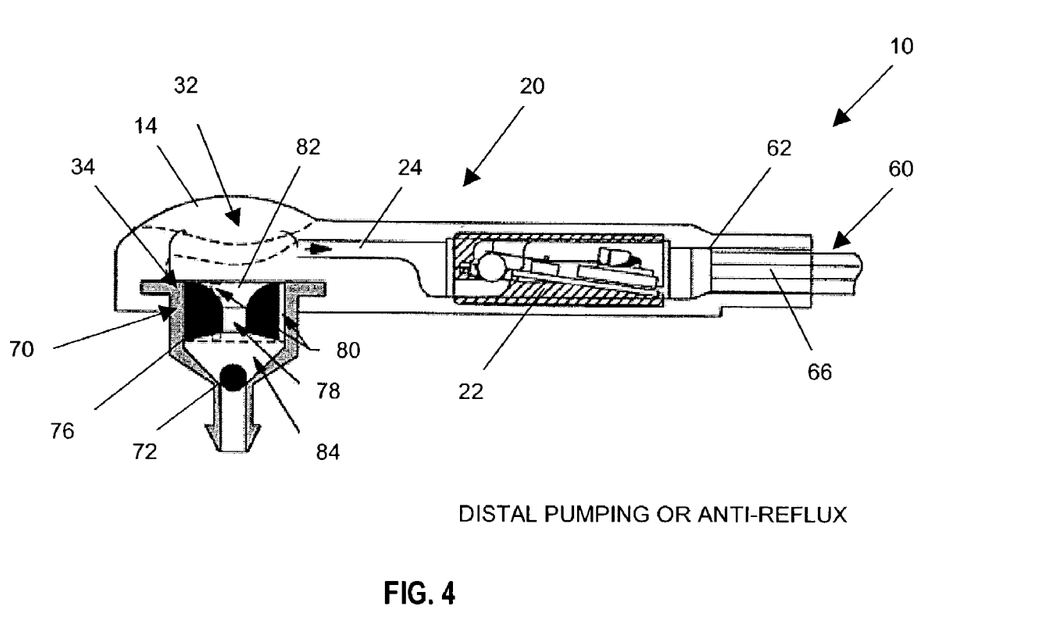
FIG. 4 is a cutaway side view of the shunt device during distal pumping.
Figure 5A:
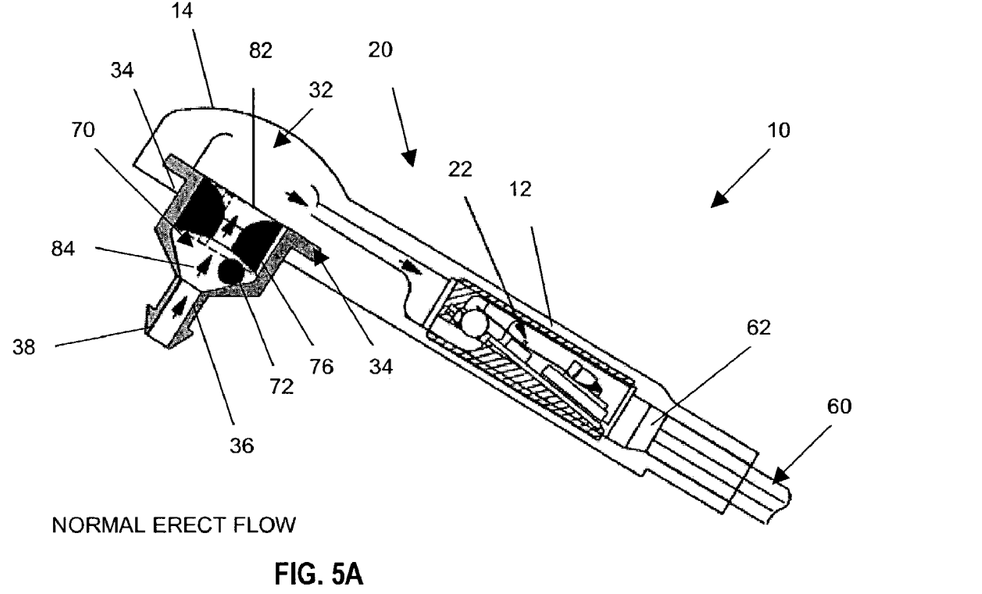
FIG. 5A is a cutaway side view of the shunt device of FIG. 3 during normal erect flow.

To allow pumping of the valve mechanism 22 distally while preventing occlusion of the shunt device 20 proximally, the base section 34 of the reservoir 30 can include a check valve mechanism 70 as illustrated in FIG. 4. Within the base section 34 are partitions 76 that form a funnel entrance 82 leading into a constricted region or central flow channel 78 that extends into the main chamber 84. The partitions 76 can be held a distance apart from the base section 34 to thereby create peripheral flow channels 80 as well. The peripheral flow channels 80 lend anti-siphon properties to the check valve mechanism 70 by creating narrow structures that restrict fluid flow distally. A free floating ball 72 is provided with the check valve mechanism 70 to occlude fluid flow into the base section 34 from the inflow catheter 40 during distal pumping or anti-reflux as shown in FIG. 4. The free floating ball 72 can be pushed aside or manipulated aside by positioning the patient, such as in FIG. 5A where normal flow conditions are present and fluid flows from the inflow catheter 40 through the base section 34 of the reservoir 30 and to the valve mechanism 22 as indicated by the arrows.

Figure 5B:
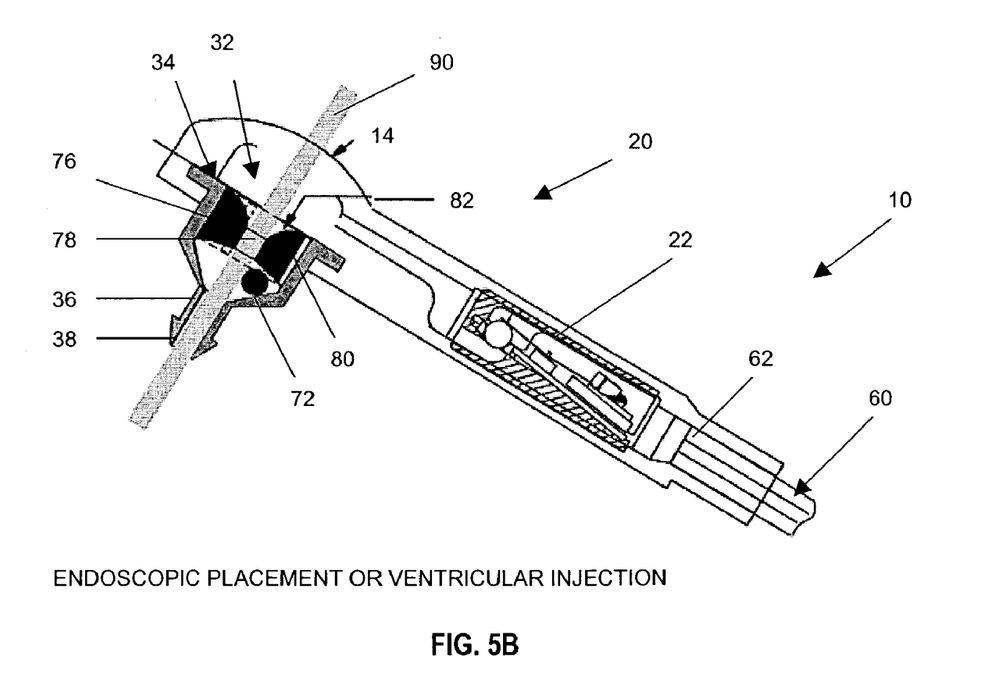
FIG. 5B is a cutaway side view of the shunt device of FIG. 3 during endoscopic placement or ventricular injection.

The free floating ball 72 can also be pushed aside using an endoscope 90 such as in FIG. 5B during endoscopic placement of the shunt system 10 or during ventricular injection. To provide the endoscope 90 with access to the check valve mechanism 70, the domed cap 14 of the housing 12 can include an endoscope port 16. The endoscope port 16 can comprise a pre-formed slit comprising a resealable silicone and can extend into a portal 18 that connects to the top section 32 of the reservoir. Once the endoscope 90 has passed through the portal 18, the endoscope can continue through the top section 32 and into the base section 34 past the central flow channel 78. The endoscope 90 can extend all the way out through the catheter connector 36 to facilitate placement of the shunt device 20 with respect to the pre-inserted inflow catheter 40 and allow endoscopic visualization as needed. The endoscope port 16 can also include radiopaque markings to assist the surgeon in locating and targeting the port 16.

Figure 6A:
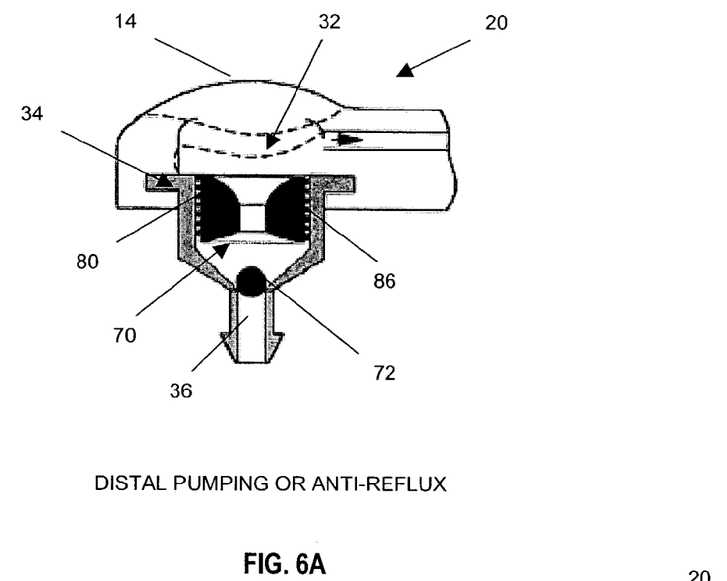
FIG. 6A is a cutaway side view of another embodiment of the base section during distal pumping.
Figure 6B:
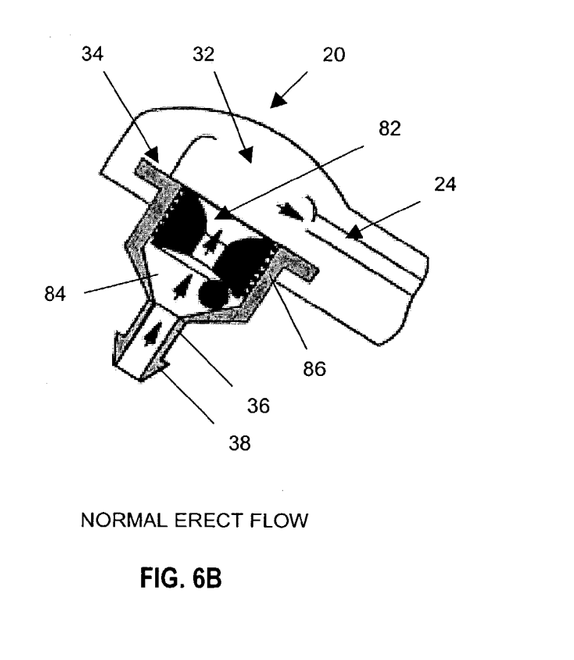
FIG. 6B is a cutaway side view of the base section of FIG. 5A during normal erect flow.
Figure 6C:
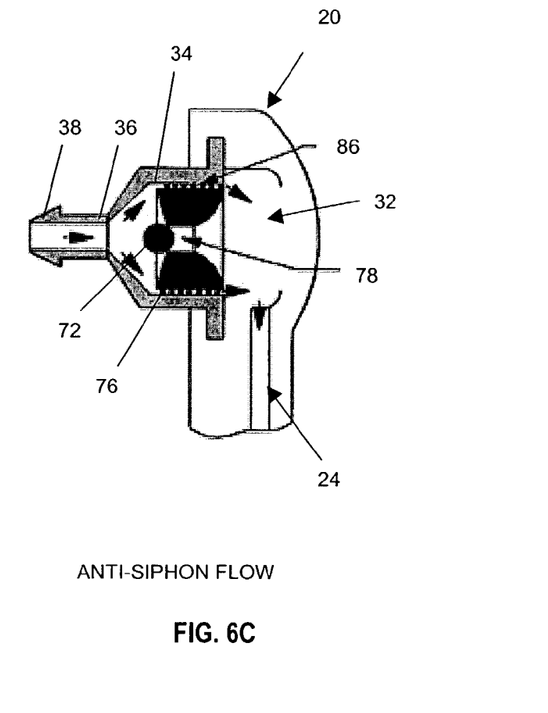
FIG. 6C is a cutaway side view of the base section of FIG. 5A during anti-siphon flow.
Figure 6D:
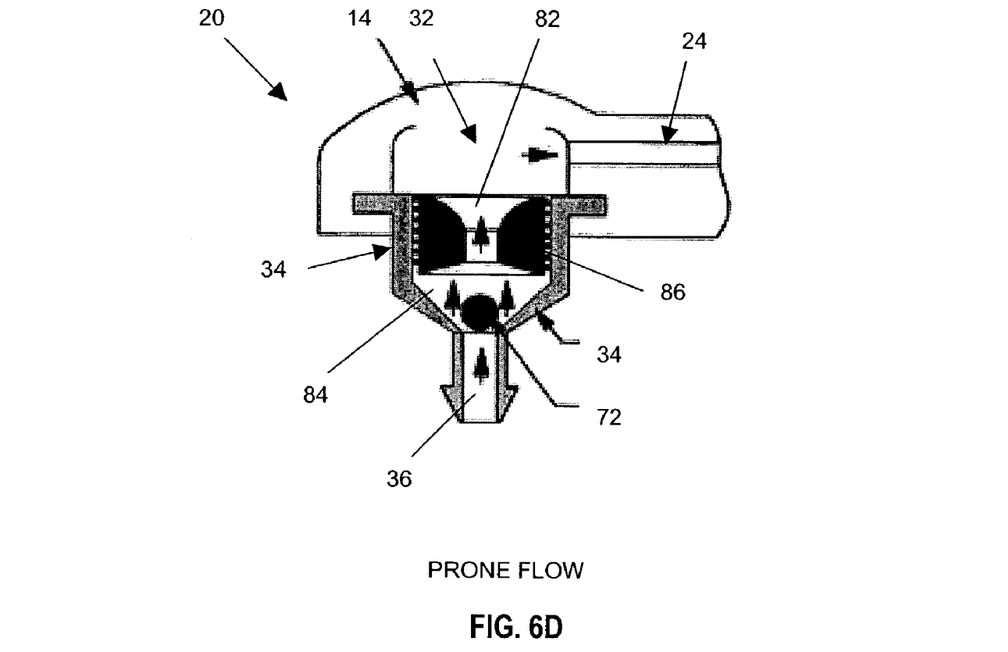
FIG. 6D is a cutaway side view of the base section of FIG. 5A during prone flow.
Figure 6E:
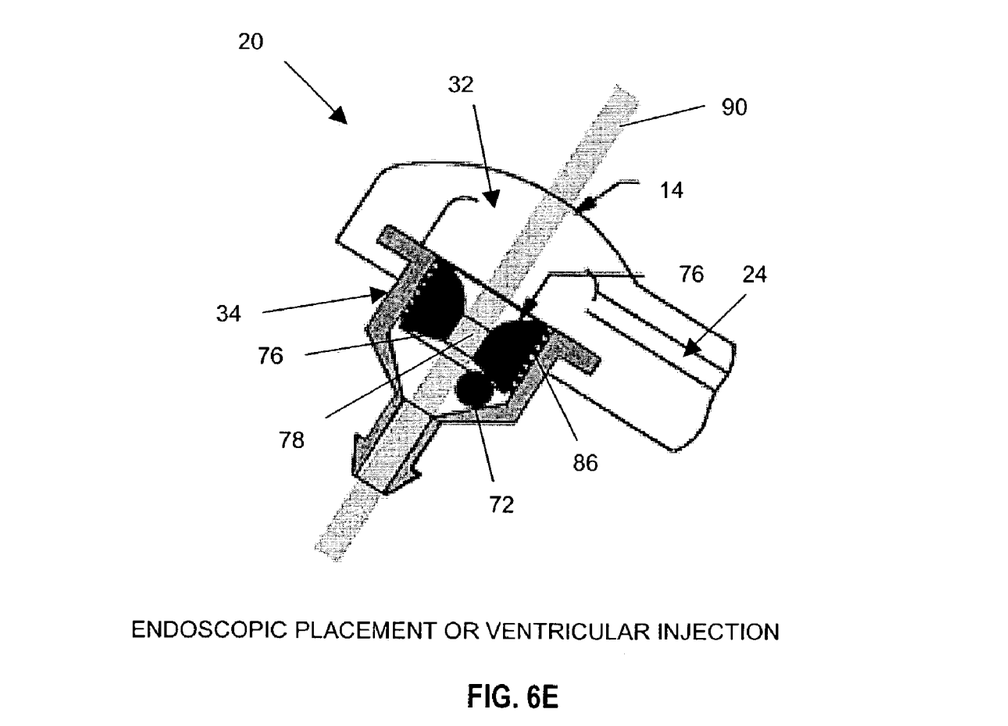
FIG. 6E is a cutaway side view of the base section of FIG. 5A during endoscopic placement or ventricular injection.

Additionally, the peripheral flow channels 80 of the base section 34 can be made more tortuous with surface features such as helical ridges 86 as illustrated in FIG. 6A which shows the flow dynamics during distal pumping or anti-reflux. The helical ridges 86 within the peripheral flow channels 80 provide the shunt system 10 with higher resistance and even more anti-siphoning capabilities. FIG. 6B shows the flow dynamics during normal erect flow, while FIG. 6C shows the flow dynamics during anti-siphon flow in which fluid traveling distally is forced through the tortuous path of the peripheral flow channels 80 and is thereby drained from the shunt system 10 at a reduced rate. Finally, the flow dynamics during prone flow, or during distal pumping is illustrated in FIG. 6D, while FIG. 6E shows the use of an endoscope 90 with the present shunt system 10 during endoscopic placement or ventricular injection.

Figure 7:
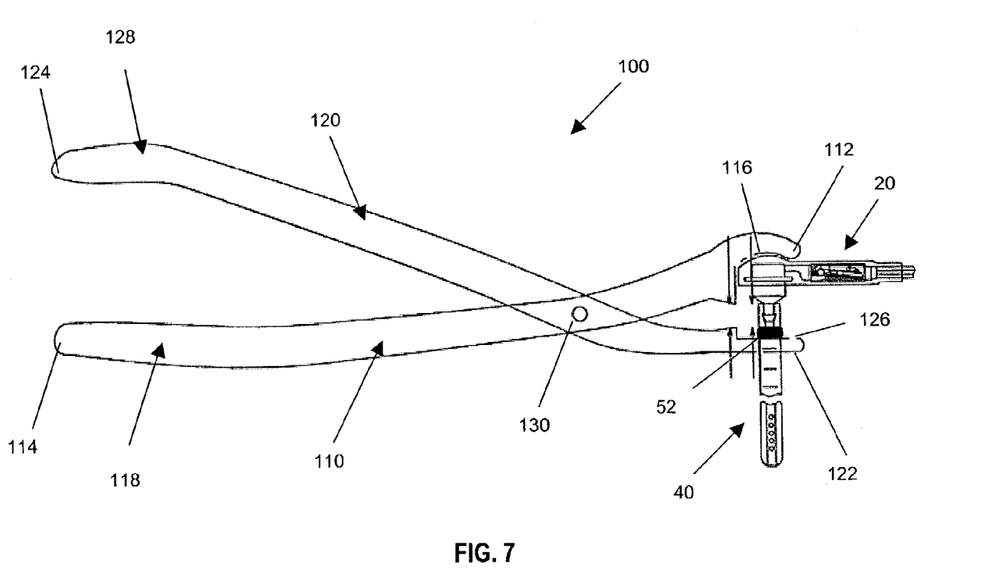
FIG. 7 is a perspective view of an instrument for assembling the shunt system of the present invention.

The present invention also provides an instrument 100 for assembling the inflow catheter 40 quickly and easily to the shunt device 20. The instrument 100 has a first arm 110 having a proximal end 112 and a distal end 114 including a handle portion 118. Pivotally connected to the first arm 110 at pin 130 is a second arm 120 having a proximal end 122 and a distal end 124 including a handle portion 128. The proximal end 112 of the first arm 110 includes a gripping section 116 that is configured to hold a portion of the housing 12. As illustrated in FIG. 7, the gripping portion 116 is configured to seat against the domed cap 14 of the housing 12. The proximal end 122 of the second arm also includes a platform section 126 that is configured to sit around the inflow catheter 40 and against the retaining ring 52 while resting on the patient's scalp. Upon compressing the handle portions 118, 128 together, the gripping section 116 and platform section 126 advance towards each other, in the process forcing the retaining ring 52 up towards the first, attachment end 42 of the inflow catheter 40. The platform section 126 is configured to slide along the inflow catheter 40. The use of the instrument 100 to connect these components enables the retaining ring 52 to slide over the attachment end 42 of the ventricular catheter 40 and over the flange 38 of the connector 36 without over advancement.

Typically, the outflow catheter 60 can be assembled to the shunt device 20 prior to implantation, while the inflow catheter 40 is assembled to the shunt device after the two components are separately implanted. In one exemplary embodiment of the shunt system 10, when fully assembled the inflow catheter extends at approximately 90° with respect to the outflow catheter.

The endoscopic placement features just described for the shunt system 10 of the present invention allow the system 10 to be easily assembled and implanted using endoscopic placement so as to require only minimally invasive surgery. The assembly process for the present invention minimizes surgery time and avoids leakage at the connection sites, since the retaining ring eliminates the need for suturing methods. The endoscopic placement features of the present invention also provides the added benefits of revision on a minimally invasive basis, such as clearing or draining obstacles to improve cerebrospinal fluid flow, without major surgical intervention. Finally, the check valve mechanism of the reservoir also provides easy occlusion for distal flushing. All of these features make endoscopic placement more convenient for the surgeon, and provide a better and more effective shunt system for the patient.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A shunt system for draining fluid within a patient, comprising:
   a housing containing a shunt device having a valve mechanism therein for regulating fluid flow into and out of the shunt system, a pump chamber in fluid communication with the valve mechanism, and a reservoir connected to and fluidly communicating with the pump chamber, the reservoir including a top section and a base section extending into a connector, wherein at least a portion of the connector extends out of the housing;
   an inflow catheter having a first end configured for attachment to the connector, a second end configured for fluid uptake, and a channel extending therebetween for carrying fluid within the inflow catheter, the inflow catheter further including a locking mechanism adapted to secure the first end to the connector, the locking mechanism being configured to move between a locked and unlocked position; and
   an outflow catheter having a first end configured for attachment to the valve mechanism, a second end configured for fluid release, and a channel extending therebetween for carrying fluid within the outflow catheter.

2. The system of claim 1, wherein the connector includes a flange.

3. The system of claim 2, wherein the attachment end of the inflow catheter is configured to provide an interference fit with the flange of the connector.

4. The system of claim 3, wherein an inner diameter of the inflow catheter at the attachment end is dimensioned to form an interference fit with the flange of the connector.

5. The system of claim 4, wherein the locking mechanism comprises a retaining ring for maintaining the attachment end of the inflow catheter onto the connector.

6. The system of claim 5, wherein the retaining ring is configured to slide along the inflow catheter and towards the attachment end of the inflow catheter when the attachment end is fitted onto the connector.

7. The system of claim 5, wherein the retaining ring is secured to the inflow catheter at the attachment end.

8. The system of claim 7, wherein the retaining ring is secured to an outer diameter of the inflow catheter.

9. The system of claim 7, wherein the retaining ring is secured to the inner diameter of the inflow catheter at the attachment end.

10. The system of claim 6, wherein the inflow catheter and outflow catheter extend at a 90° angle with respect to one another.

11. The system of claim 10, further including an instrument for connecting the inflow catheter to the connector of the base section.

12. The system of claim 11, wherein the instrument comprises:
   a first arm having a proximal end including a gripping section configured for holding a portion of the housing, and a distal end including a handle portion; and
   a second arm having a proximal end including a platform section configured to sit around the inflow catheter and against the retaining ring, and a distal end including a handle portion, the second arm being pivotally connected to the first arm;
   wherein compressing the handle portions together advances the retaining ring towards the attachment end of the inflow catheter.

13. The system of claim 12, wherein the platform is configured to slide along the inflow catheter.

14. The system of claim 1, wherein the inflow catheter includes indicia thereon, the indicia representing the length of the catheter.

15. The system of claim 1, wherein the inflow catheter includes at least one aperture near the fluid uptake end.

16. The system of claim 1, wherein the fluid uptake end of the inflow catheter is closed, and further includes a pre-formed slit.

17. The system of claim 1, wherein the housing includes a domed cap.

18. The system of claim 17, wherein the domed cap includes an endoscope port, the endoscope port further comprising a pre-formed slit.

19. The system of claim 18, wherein the endoscope port is radiopaque.

20. The system of claim 18, wherein the endoscope port is formed from resealable silicone.

21. The system of claim 1, wherein the base portion of the reservoir includes a check valve mechanism.

22. The system of claim 21, wherein the check valve mechanism includes a free floating ball.

23. The system of claim 1, wherein the base portion includes peripheral flow channels.

24. The system of claim 23, wherein the peripheral flow channels include surface features that provide resistance to fluid flow therethrough.

25. The system of claim 24, wherein the surface features include helically arranged ridges.

26. A shunt system for draining fluid within a patient, comprising:
   a housing containing a shunt device having a valve mechanism therein for regulating fluid flow into and out of the shunt system, a pump chamber in fluid communication with the valve mechanism, and a reservoir connected to and fluidly communicating with the pump chamber, the reservoir including a top section and a base section extending into a connector, wherein at least a portion of the connector extends out of the housing;
   an inflow catheter having a first end configured for attachment to the connector, a second end configured for fluid uptake, and a channel extending therebetween for carrying fluid within the inflow catheter, the inflow catheter further including a locking mechanism configured to move between a locked and unlocked position and adapted to secure the first end to the connector; and
   an outflow catheter having a first end configured for attachment to the valve mechanism, a second end configured for fluid release, and a channel extending therebetween for carrying fluid within the outflow catheter,
   wherein the locking mechanism includes a retaining ring configured to slide along the inflow catheter and towards the attachment end of the inflow catheter when the attachment end is fitted onto the connector.

* * * * *